United States Patent
Militello

(10) Patent No.: US 7,330,759 B2
(45) Date of Patent: Feb. 12, 2008

(54) BIVENTRICULAR CARDIAC PACEMAKER FOR CARDIAC RESYNCHRONISATION THERAPY

(75) Inventor: Carmelo Militello, Rome (IT)

(73) Assignee: BIOTRONIK GmbH & Co., Berlin (DE)

( * ) Notice: Subject to any disclaimer, the term of this patent is extended or adjusted under 35 U.S.C. 154(b) by 114 days.

(21) Appl. No.: 10/537,703

(22) PCT Filed: Nov. 28, 2003

(86) PCT No.: PCT/EP03/13450

§ 371 (c)(1),
(2), (4) Date: Dec. 12, 2005

(87) PCT Pub. No.: WO2004/050177

PCT Pub. Date: Jun. 17, 2004

(65) Prior Publication Data

US 2006/0142811 A1 Jun. 29, 2006

(30) Foreign Application Priority Data

Dec. 2, 2002 (DE) ............... 102 57 156

(51) Int. Cl.
*A61N 1/365* (2006.01)
*A61B 5/02* (2006.01)

(52) U.S. Cl. ........................... 607/17; 600/508

(58) Field of Classification Search ............ 607/9, 607/17; 600/508
See application file for complete search history.

(56) References Cited

U.S. PATENT DOCUMENTS

| 4,773,401 A | * | 9/1988 | Citak et al. .................. 607/17 |
|---|---|---|---|
| 5,782,884 A | | 7/1998 | Stotts et al. |
| 5,902,325 A | | 5/1999 | Condie et al. |
| 6,070,100 A | * | 5/2000 | Bakels et al. .................. 607/9 |
| 6,134,472 A | | 10/2000 | Strandberg et al. |
| 6,219,579 B1 | * | 4/2001 | Bakels et al. ................. 607/17 |
| 6,223,079 B1 | * | 4/2001 | Bakels et al. .................. 607/9 |
| 6,223,082 B1 | * | 4/2001 | Bakels et al. ................. 607/17 |
| 6,238,420 B1 | | 5/2001 | Bakels et al. |
| 6,263,243 B1 | | 7/2001 | Lang |

(Continued)

FOREIGN PATENT DOCUMENTS

EP 0793976 9/1997

(Continued)

*Primary Examiner*—Angela D. Sykes
*Assistant Examiner*—Christopher A. Flory
(74) *Attorney, Agent, or Firm*—Hahn Loeser & Parks, LLP; John J. Cunniff

(57) ABSTRACT

The invention concerns a cardiac pacemaker comprising a stimulation pulse generator (RVP; LVP) for biventricular stimulation of a heart, which is to be connected to at least one right-ventricular electrode for the stimulation of a right ventricle of the heart and to at least one left-ventricular electrode for the stimulation of a left ventricle of the heart and is connected to a control unit and is adapted to trigger right-ventricular and left-ventricular stimulation pulses with an interventricular delay time which is adjustable by means of the control unit. The invention is characterized in that the control unit is connected to an impedance detection unit which is to be connected to intercardiac electrodes and is adapted to form from an input signal formed by the impedance detection unit and dependent on the intracardiac impedance, an output signal indicating an optimum biventricular stimulation mode.

20 Claims, 4 Drawing Sheets

U.S. PATENT DOCUMENTS

| | | |
|---|---|---|
| 6,278,894 B1 | 8/2001 | Salo et al. |
| 6,339,724 B1 * | 1/2002 | Thong .......................... 607/28 |
| 6,505,070 B1 * | 1/2003 | Backers ......................... 607/9 |
| 6,522,923 B1 * | 2/2003 | Turcott ......................... 607/27 |
| 6,556,866 B2 * | 4/2003 | Dal Molin et al. ............. 607/9 |
| 6,567,700 B1 * | 5/2003 | Turcott et al. ................. 607/9 |
| 6,708,061 B2 * | 3/2004 | Salo et al. ..................... 607/9 |
| 6,725,091 B2 * | 4/2004 | Dal Molin ..................... 607/2 |
| 6,792,310 B1 * | 9/2004 | Turcott et al. ................ 607/27 |
| 2001/0012953 A1 | 8/2001 | Molin et al. |
| 2001/0049542 A1 | 12/2001 | Florio et al. |
| 2004/0127944 A1 * | 7/2004 | Casset ........................... 607/4 |
| 2005/0038481 A1 * | 2/2005 | Chinchoy et al. ............. 607/17 |
| 2005/0049646 A1 * | 3/2005 | Czygan et al. ................ 607/27 |
| 2005/0125042 A1 * | 6/2005 | Noren et al. .................. 607/17 |
| 2005/0240233 A1 * | 10/2005 | Lippert et al. ................. 607/6 |

FOREIGN PATENT DOCUMENTS

| | | |
|---|---|---|
| WO | WO 9930777 | 6/1999 |
| WO | WO 0078391 | 12/2000 |
| WO | WO 03051457 | 6/2003 |

* cited by examiner

BIVENTRICULAR CARDIAC PACEMAKER FOR CARDIAC RESYNCHRONISATION THERAPY

The invention concerns a cardiac pacemaker comprising a stimulation pulse generator for biventricular stimulation of a heart. The stimulation pulse generator is to be connected to right-ventricular electrodes for the stimulation of a right ventricle of the heart and to left-ventricular electrodes for the stimulation of a left ventricle of the heart. Instead of a stimulation pulse generator, it is also possible to provide two separate stimulation pulse generators for the right and left ventricles. The cardiac pacemaker also has a control device, for example in the form of a control unit, which is connected to the stimulation pulse generator or the ventricular stimulation pulse generators and which is adapted to control biventricular stimulation modes and in particular an interventricular delay time which is adjustable by the control device, with which right-ventricular and left-ventricular stimulation pulses are to be triggered in time-delayed relationship.

BACKGROUND OF THE ART

Pacemakers of that kind for biventricular stimulation are basically known and are employed in particular for cardiac resynchronization therapy (CRT).

Cardiac pacemakers generally serve to stimulate in particular a human heart to perform contractions by means of electrical stimulation pulses when such contractions do not occur or do not occur at the correct time, in a natural manner.

It is known to establish moments in time or time windows at which such a cardiac pacemaker expects a natural contraction. If a natural contraction of that kind occurs, an artificial stimulation pulse is generally suppressed (inhibited), which otherwise is delivered at the most appropriate moment in time. It is also known, under given circumstances and depending on the mode of operation of the cardiac pacemaker, to deliver a stimulation pulse at any event, irrespective of whether a natural contraction is or is not detected. The pacemaker operating modes related thereto are uniformly internationally identified by the third letter of a three-letter code such as "VVI" or "DDD".

Suitable moments in time can be ascertained in various different ways. For example, the physiologically suitable times for a contraction of the right ventricle of a heart can be ascertained by sensing the right atrium of a heart. The natural or the stimulated contraction of the right ventricle takes place after an atrio-ventricular delay time which is such as to afford a pump effectiveness which is as optimum as possible due to the contraction of the atrium and the ventricle which occur in succession in respect of time.

In addition it is also known if necessary to stimulate the atrium.

The heart rate which is predetermined by the pacemaker can in all cases be derived artificially from a measurement value which is characteristic in respect of the physiological demand of a patient if it is not predetermined in the case of atrium-synchronous stimulation by a natural and healthy atrial rhythm. In that respect the physiological demand depends on a condition of exertion or excitation on the part of the patient. In the case of a rate-adaptive pacemaker of that kind, physiologically adequate determination of a stimulation rate can also be effected by determining the intracardiac impedance for a respective cardiac cycle and deriving a suitable stimulation rate from that impedance value.

The indicated operating modes generally concern pacemakers which are either adapted to record excitation potential in the right ventricle and deliver stimulation pulses to a right ventricle or additionally also to record excitation potential in the right atrium and possibly deliver stimulation pulses to the right atrium. The pacemaker operating modes related thereto are internationally uniformly identified by the three-letter code such as for example DDD or VVI.

In recent times, besides the right atrium and the right ventricle, the left ventricle is also stimulated. That is frequently effected simultaneously with the right ventricle, but can also take place with a certain delay relative to the left ventricle. A cardiac pacemaker therapy for the heart, which is linked thereto, is referred to as cardiac resynchronization therapy (CRT).

A biventricular pacemaker in which the interventricular delay time is adjustable and which evaluates a measured bioimpedance of the patient is known from US Patent Publication No 2001/0012953.

The invention relates in particular to the aspect of optimum biventricular stimulation, which can supplement all the above-indicated aspects of a pacemaker. The object of the invention is in particular to provide a pacemaker for optimized cardiac resynchronization therapy.

SUMMARY OF THE INVENTION

In accordance with the invention, that object is attained in that the control unit of the pacemaker of the kind set forth in the opening part of this specification is connected to an impedance detection unit which is to be connected to intracardiac electrodes for the purposes of impedance measurement. The impedance detection unit is adapted to form an output signal indicating an optimum biventricular stimulation mode, from an input signal which is formed by the impedance detection unit and which is dependent on the intracardiac impedance, more specifically by the control unit being adapted to adjust that interventricular delay time, to indicate that electrode position, or to indicate that univentricular or biventricular stimulation mode, at which the second derivative of the pattern of the intracardiac impedance during a cardiac cycle or the intracardiac impedance averaged over a plurality of cardiac cycles is at the greatest.

In a preferred variant, the control unit is adapted to form an output signal determining the interventricular delay time. Besides the interventricular delay time, a respective biventricular stimulation mode is also determined by whether both ventricles are stimulated in any case, or only one of the two. In that sense, the control unit is adapted to ascertain for a basically biventricular cardiac pacemaker whether it is additionally optimum to stimulate both ventricles and, if so, with what delay time. If evaluation of the intracardiac impedance by the control unit should show that only one of the two ventricles is to be stimulated, the optimum ventricle is also ascertained.

To determine the optimum biventricular stimulation mode, the control unit is preferably adapted to trigger various biventricular stimulation modes and to evaluate the intracardiac impedance for each stimulation mode. The various stimulation modes differ in respect of whether no or only a respective one of both ventricles (fake biventricular stimulation, here also referred to as univentricular stimulation) or both ventricles (genuine biventricular stimulation) are stimulated. In the case of both ventricles being stimulated, various sub-modes of the genuine biventricular stimulation mode differ by virtue of mutually differing interventricular delay times.

The invention is based on the realization that how well the left and right ventricles of a heart in biventricular cardiac pacemaker therapy are synchronized with each other, in particular in the context of resynchronization therapy, is to be gauged from the intracardiac impedance, more specifically in particular the second derivative thereof. It is from that new realization that the teaching is derived, of evaluating measurement results for the intracardiac impedance in particular for the purposes of optimizing the interventricular delay time. That makes it possible to automate not only ascertainment but also adjustment of the parameters of an optimum biventricular stimulation within a cardiac pacemaker, by a control unit evaluating intracardially detected impedance values and deriving therefrom a control signal which determines the stimulation parameters, in particular the interventricular transconduction time.

As an alternative to cardiac pacemaker-internal, automatic determination of the optimum biventricular mode, it is also possible and provided that the control unit generates from the measurement values for intracardiac impedance for various interventricular delay times an output signal which indicates the physiologically most appropriate one of the various interventricular delay times. That output signal is preferably telemetrically transmitted to an external device and displayed to a physician in each case together with the associated biventricular stimulation mode, in particular the interventricular delay time. The physician can then also telemetrically optimally adjust the interventricular delay time on the basis of the displayed output signals.

Preferably the interventricular delay time can be adjusted at between 20 and 40 ms.

Alternatively or additionally the control unit is adapted, with different electrode configurations or electrode positions, to derive corresponding output signals from the measurement values in respect of intracardiac impedance. Those output signals are preferably also telemetrically transmitted to an extracorporeal device and displayed there. That makes it possible for a physician for example, when already involved in the operation of implanting the right-ventricular and/or the left-ventricular electrode, to position it in the optimum manner, having regard to the intracardially detected impedance values.

In the case of electrode lines having a plurality of electrodes which can be associated with the ventricular stimulation generator, it is possible for the optimally effective electrode configuration to be determined by means of the measured impedance values. That can be effected as described hereinabove by a physician by means of external programming of the optimum electrode configuration by telemetric means. For that purpose the output signal ascertained from the intracardiac impedance values by the control unit is telemetrically transmitted to an extracorporeal device and displayed there. However, the operation of determining the optimum electrode configuration can also be effected automatically within the cardiac pacemaker by the control unit being connected to a selection unit for the ventricular stimulation electrodes in question, and actuating that selection unit in dependence on the detected intracardiac impedance values.

In alternative preferred embodiments, the control unit is adapted to derive precisely the output signal for adjusting the optimum interventricular delay time or alternatively an output signal for determining an optimum electrode position or configuration from the second derivative of the intracardiac impedance pattern of a cardiac cycle. Alternatively, the control unit can also be adapted to derive the output signal referred to in the previously mentioned paragraph solely from the maximum value of the impedance during a cardiac cycle.

For intracardiac impedance measurement, it is preferably provided that the impedance is ascertained by measuring a voltage between two intercardiac electrodes. Those two electrodes are preferably disposed on various electrode lines, more specifically on the one hand being associated with the left ventricle and on the other hand with the right ventricle. A measurement current which is the cause of the above-mentioned voltage to be measured is preferably produced between two electrodes which are different from the electrodes for voltage measurement. Preferred electrodes for introducing the preferably constant measurement current are on the one hand the pacemaker housing and on the other hand a further intercardiac electrode which is preferably arranged on the electrode line of the right ventricle.

The current for impedance measurement is preferably of a substantially constant current strength of between 100 and 500 mA, preferably 200 mA. The current for impedance measurement is preferably specified in bi-phase current pulses. The duration of a current pulse is preferably between 20 and 40 microseconds, particularly preferably being 30 microseconds. The current pulses are preferably repeated at a repetition rate of between 100 and 150 Hertz, preferably being 128 Hertz.

The impedance detection unit is preferably adapted to ascertain the impedance in a time window of between 50 and 300 ms in duration. That time window is preferably started with the detection of a left-ventriculating event. A left-ventricular event is for example a natural contraction of the left ventricle or also a superthreshold stimulation pulse to the left ventricle.

Preferably, the impedance detection unit is adapted to detect an averaged impedance pattern over a plurality of cardiac cycles. In that case, the respective stimulation mode is kept constant over the cardiac cycles to be averaged. The detected intracardiac impedance pattern is preferably subjected to low pass filtering by the impedance detection unit, more specifically with an upper limit frequency of preferably 10 Hz.

The intracardiac impedance pattern obtained in that way by averaging and low pass filtering is evaluated by the control unit by the second derivative being formed from that impedance pattern. On the assumption that the intracardiac impedance pattern respectively reflects the volume of blood in a heart, the maximum acceleration to which the blood is subjected in the heart is to be gauged from the maximum of the second derivative of that intracardiac impedance pattern. That value can be correlated to contractility of the left ventricle.

In addition, the impedance detection unit or the control unit is adapted to determine one or more of the following parameters from the intracardiac impedance configuration:

$Z_{ED}$ as a base line for the impedance pattern, $Z_{ES}$ as the maximum impedance occurring within a cardiac cycle, $T_{ES}$ as the spacing in respect of time between a QRS complex (beginning of the contraction of the heart) and the moment in time at which the maximum intercardiac impedance $Z_{ES}$ occurs, $Z_{min}$ as the minimum impedance during a cardiac cycle, and $T_{min}$ as the period of time beginning with a QRS complex to the occurrence of the minimum intracardial impedance $Z_{min}$.

In addition, the impedance detection unit or the control unit is adapted to ascertain derived values from the above-mentioned values, namely:

the difference ($Z_{ES}-Z_{ED}$) between the maximum impedance $Z_{ES}$ and the base line impedance $Z_{ED}$, the difference ($Z_{ES}-Z_{min}$) between the maximum detected impedance $Z_{ES}$ and the minimum detected impedance $Z_{min}$ (impedance variation during a cardiac cycle), and the quotient (($Z_{ES}-Z_{min}$)/$T_{ES}$) of the impedance variation ($Z_{ES}-Z_{min}$) and the time $T_{ES}$, and the quotient (($Z_{ES}-Z_{min}$)/$T_{ES}-T_{min}$)), formed by the impedance variation ($Z_{ES}-Z_{min}$) divided by the difference ($T_{ES}-T_{min}$) between $T_{ES}$ and $T_{min}$, the maxima $Z'_{max}$ and $Z''_{max}$ of the first and second derivatives of the intracardiac impedance, and the respective time spacings $T'_{max}$ and $T''_{max}$ beginning with a QRS complex to the moment in time at which a maximum in respect of the first and second derivative respectively of intracardiac impedance occurs.

In addition, the cardiac pacemaker is preferably in the form of a dual-chamber cardiac pacemaker which includes atrial and ventricular stimulation units as well as atrial and ventricular detection units for detecting ventricular and atrial events respectively.

In addition, the pacemaker is preferably in the form of a rate-adaptive pacemaker in which the stimulation rate is controlled by a measurement value characteristic of the physiological demand of a patient.

Particularly preferred is a rate-adaptive cardiac pacemaker in which the stimulation rate is adjusted on the basis of evaluation of the intracardiac impedance. That concept is known as closed-loop stimulation and is based on evaluation of intracardiac impedance by integral formation.

Also preferred is a cardiac pacemaker having means for detecting stimulation success (capture control). Those means are preferably adapted also to respond to the intracardiac impedance pattern.

For a cardiac pacemaker which affords the presented optimization of the biventricular stimulation mode by evaluation of intracardiac impedance, in the situation where it further involves rate adaptation in the sense of closed-loop stimulation (evaluation of the integral of intracardiac impedance) and possibly also an impedance-based stimulation success check (capture control), there is also the advantage that a large number of procedures are controllable in a cardiac pacemaker, with an impedance detection unit.

BRIEF DESCRIPTION OF THE DRAWINGS

The invention will now be described in greater detail by means of embodiments by way of example with reference to the drawings in which.

DETAILED DESCRIPTION OF THE INVENTION

Figure 1A:
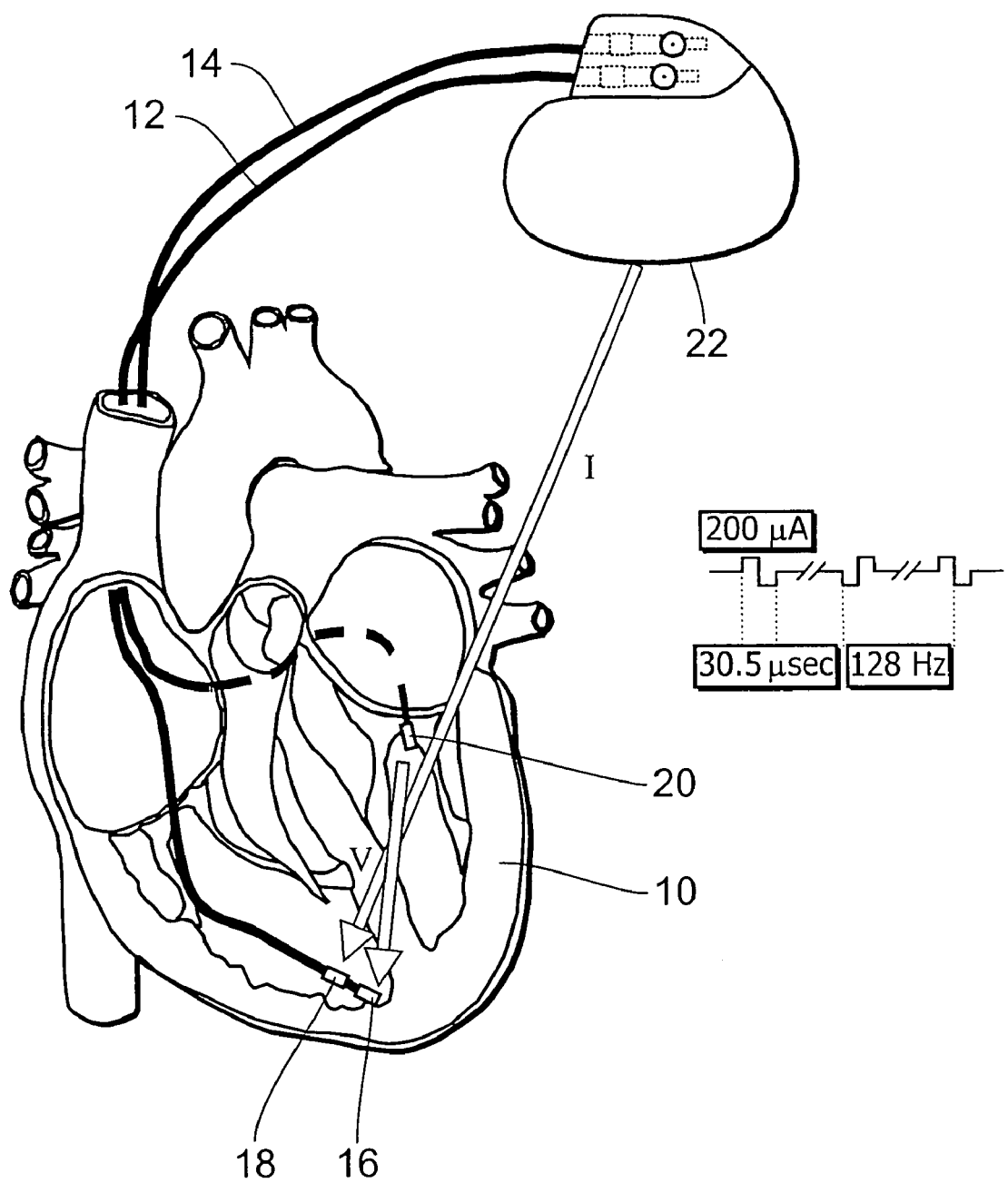
FIGS. 1a and 1b each show an overview of a human heart with implanted electrode lines and cardiac pacemaker connected thereto.
Figure 1B:
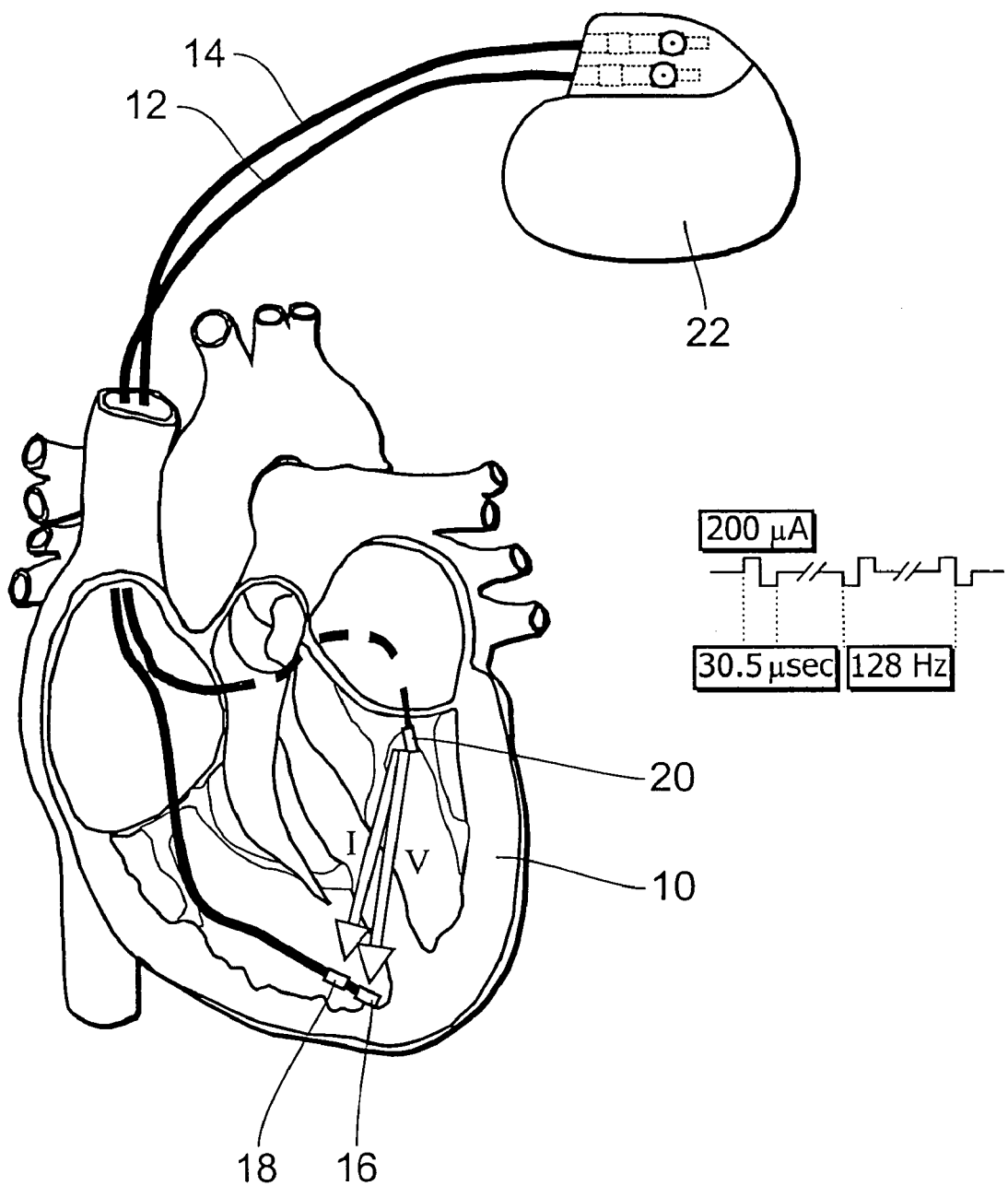

FIGS. 1a and 1b show a human heart 10 into which in each case a right-ventricular electrode line 12 and a left-ventricular electrode line 14 is intracardially introduced. The right-ventricular electrode line 12 is provided at the distal end with two electrodes, namely a tip electrode 16 and a ring electrode 18. The right-ventricular electrode line 12 can also have in the region of the atrium atrial stimulation and sensing electrodes which are not shown in the illustrated embodiment.

The left-ventricular electrode line 14 is introduced by way of the coronary sinus of the heart 10 and a lateral side branch which branches from that coronary sinus, so that a tip electrode 20 of the left-ventricular electrode line 14 bears against the left ventricle of the heart 10. Both electrode lines are connected to a cardiac pacemaker 22.

In FIGS. 1a and 1b, arrows show current paths and voltage measuring paths which connect together those electrodes which are used for recording the intracardiac impedance pattern for the purposes of determining the optimum biventricular stimulation mode.

FIG. 1a shows a quadropolar electrode arrangement in which the pacemaker housing and the right-ventricular ring electrode 18 serve for the introduction of a two-phase pulsed current for impedance measurement while voltage measurement for determining impedance takes place between the left-ventricular electrode 20 and the right-ventricular tip electrode 16.

FIG. 1b shows an alternative tripolar arrangement in which voltage measurement takes place as in the case of the quadropolar arrangement of FIG. 1a between the left-ventricular electrode 20 and the right-ventricular tip electrode 16. The current which is of a two-phase pulsed nature is however introduced between the left-ventricular electrode 20—which thus performs a dual function—and the right-ventricular ring electrode 18.

Figure 2:
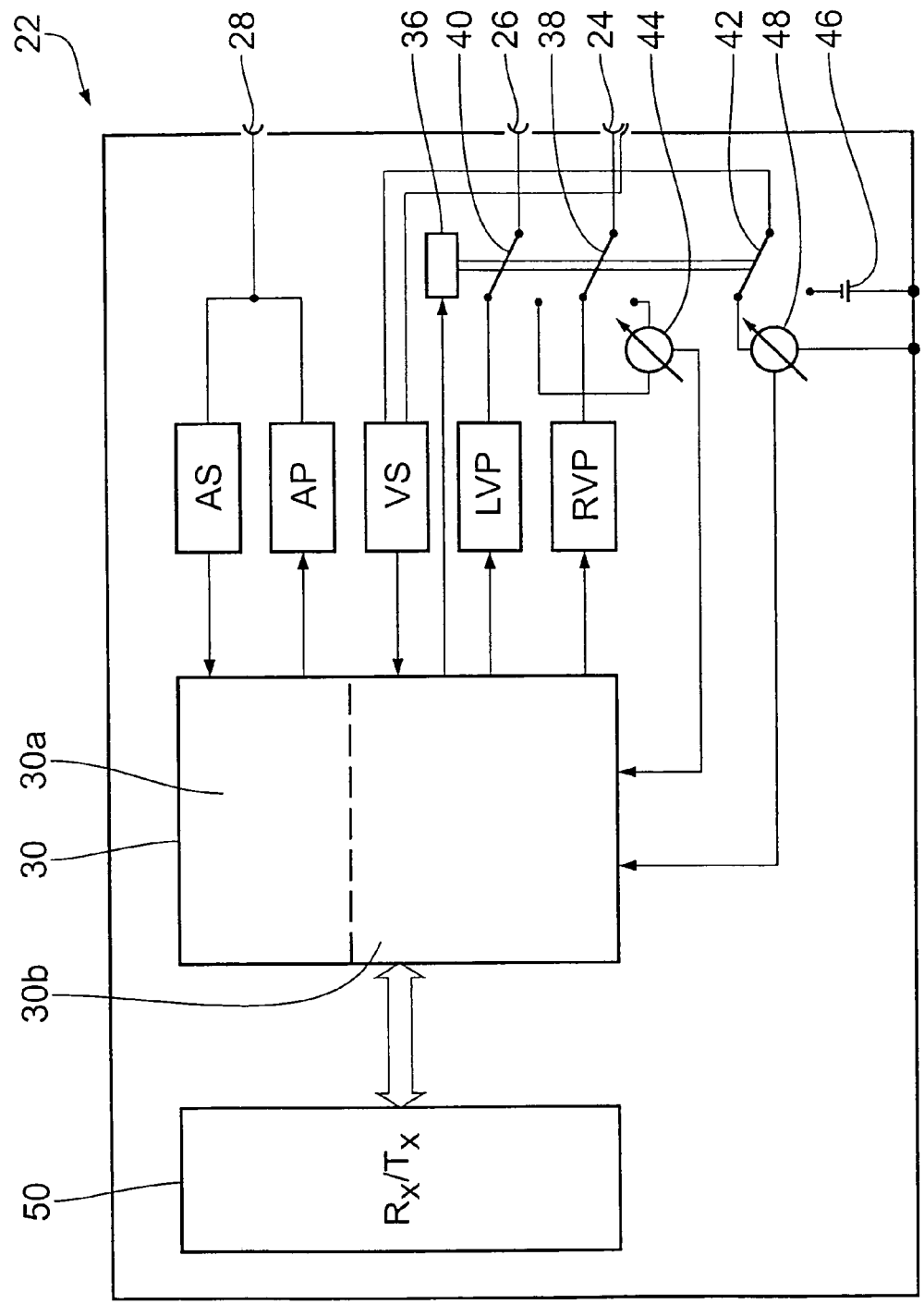
FIG. 2 shows a schematic block circuit diagram by way of example for a cardiac pacemaker as shown in FIG. 1.

FIG. 2 shows a greatly simplified block circuit diagram of the cardiac pacemaker 22. The cardiac pacemaker 22 is provided in the usual manner with connections 24 and 26 for the right-ventricular and left-ventricular electrode lines 12 and 14 respectively. The connection 24 in this case is two-poled in order separately to contact the two electrodes 16 and 18 of the right-ventricular electrode line 12. There is also an atrial electrode line connection 28. The cardiac pacemaker 22 has a right-ventricular stimulation unit RVP, a left-ventricular stimulation unit LVP, a ventricular detection unit VS, an atrial stimulation unit AP and an atrial detection unit AS. Those stimulation and detection units are connected in the manner shown in FIG. 2 on the one hand to the electrode line connections 24 through 28 and on the other hand to a control unit 30. The control unit 30 includes sub-units 30a which serve for the actuation of the atrial stimulation unit AP or for recording atrial events by means of the atrial detection unit AS.

Connected to that atrial control portion 30a is a sub-unit 30b of the control unit 30, which functions as a ventricular control portion. The ventricular control portion 30b is connected to the ventricular detection unit VS and the two ventricular stimulation units LVP and RVP. In addition the ventricular control portion is connected to an impedance detection unit 34 which is to be connected by way of a change-over switch 36 with a change-over switching contact 38 to the electrode line connection 24 and a further change-over switching contact 40 to the electrode line connection 26. That makes it possible to detect the intracardiac impedance by way of the tip electrode of the left-ventricular electrode line 14 and by way of the ring electrode of the right-ventricular electrode line 12. In one switching position of the change-over switch 36 the impedance detection unit 34 is connected to the specified electrodes while in another switching position of the change-over switch 36 the right and left ventricular stimulation units RVP and LVP are respectively connected to the specified electrodes.

A third change-over switching contact 42 serves to connect a constant current source 44 to the tip electrode of the right-ventricular electrode line 12. The other pole of the constant current source 44 is connected to the pacemaker housing. In the switching position (not shown) of the third change-over switching contact 42, a current is produced between the pacemaker housing and the tip electrode of the right-ventricular electrode line 12 by way of the constant current source 44 for impedance measurement purposes. That constant current results in a voltage drop which is to be measured by way of the impedance detection unit 34 and the tip electrode of the left-ventricular electrode line 14 as well as the ring electrode of the right-ventricular electrode line 12.

The constant current source 44 is so designed that it produces bi-phase current packets of a total of 30.5 µs in duration. Those bi-phase current pulses are repeated at a rate of 128 Hz. The current strength is sub-threshold and is preferably 200 µA.

The impedance values recorded by the impedance detection unit 44 are combined to provide an intracardiac impedance pattern which is subjected to low pass filtering with an upper limit frequency of 10 Hz.

Figure 3:
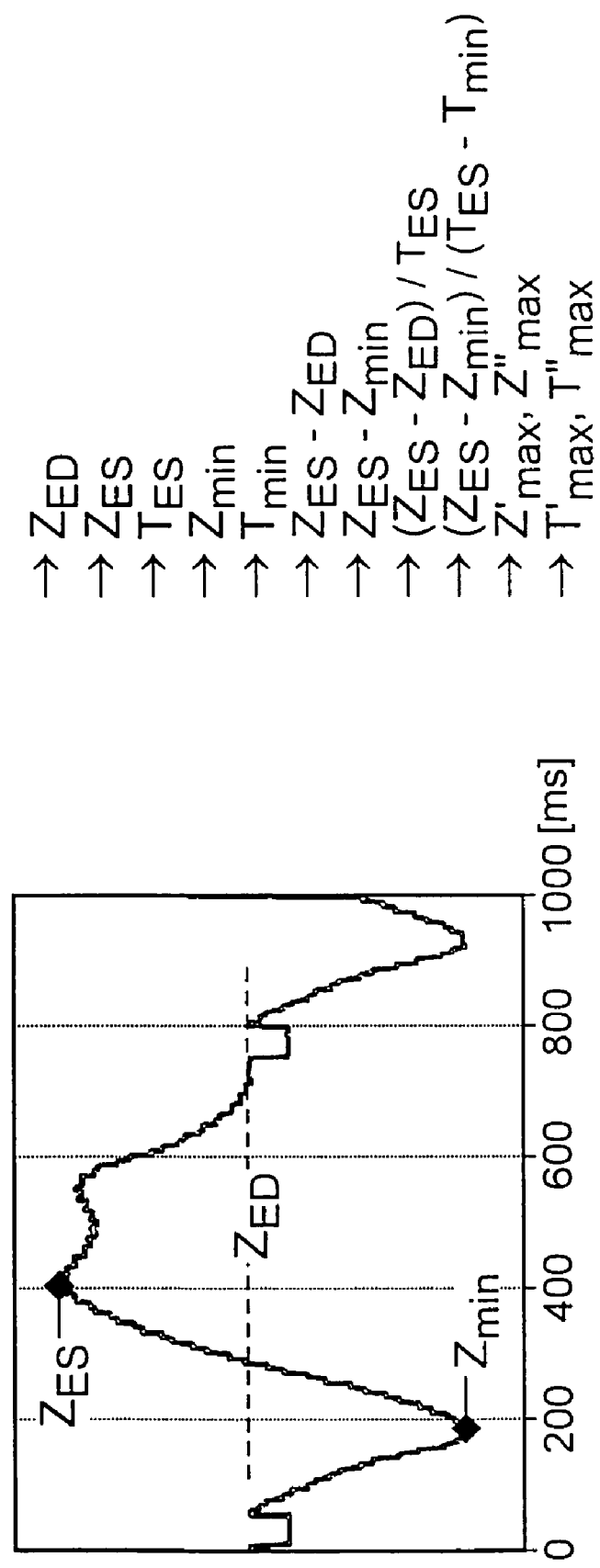
FIG. 3 shows a diagram of an intracardiac impedance pattern with a representation of the parameters derived from the intracardiac impedance pattern.

Controlled by the control unit 30, for various biventricular stimulation modes, intracardiac impedance patterns are respectively detected and averaged over a plurality of cardiac cycles (in a respective stimulation mode). The above-mentioned parameters $Z_{ED}$, $Z_{ES}$, $T_{ES}$, $Z_{min}$, $T_{min}$, $Z_{ES}-Z_{ED}$, $Z_{ES}-Z_{min}$, $(Z_{ES}-Z_{min})/T_{ES}$, $(Z_{ES}-Z_{min})/(T_{ES}-T_{min})$, $Z'_{max}$, $Z''_{max}$, $T'_{max}$ and $T''_{max}$ are formed from those averaged, low pass-filtered implants; see FIG. 3.

In each case the maximum of the second derivative of the intracardiac impedance pattern $Z''_{max}$ is stored for a respective biventricular stimulation mode. The control unit 30 determines $Z''_{max}$ for all available biventricular stimulation modes. The control unit 30 determines the maximum of that second derivative, ascertained in that way, of the intracardiac impedance pattern $Z''_{max}$ and in that way determines the associated biventricular stimulation mode as optimum.

The various stimulation modes differ in that either no or only the right, only the left or both ventricles are stimulated by way of the ventricular stimulation units LVP and RVP. In the case in which both ventricles, that is to say both the right ventricle and also the left ventricle of the heart 10, are stimulated by means of the two ventricular stimulation units RVP and LVP, the ventricular stimulation modes differ by the delay time with which the left ventricle is actuated by way of the left-ventricular stimulation unit LVP after the right ventricle by means of the right-ventricular stimulation unit RVP. In other words: firstly the right ventricle is stimulated by way of the right-ventricular stimulation unit RVP, then the interventricular delay time elapses, and finally the left ventricle is stimulated by way of the left-ventricular stimulation unit LVP.

The optimum biventricular stimulation mode ascertained in that way is automatically set by the control unit 30.

As an alternative thereto, it is also possible for the detected values to be transmitted to an extracorporeal device by way of a telemetry unit 50. In particular the extracorporeal device displays which biventricular stimulation mode is involved at the time and which is the associated value $Z''_{max}$. By way of the extracorporeal device a physician can actuate a plurality of biventricular stimulation modes and determine the associated values for $Z''_{max}$. In that way the physician can ascertain the optimum biventricular stimulation mode and set it by way of the telemetry transmitter/receiver 50 and the control unit 30.

It will be appreciated that the cardiac pacemaker 22 described herein can implement a large number of per se known functions and in particular can be operated in all known modes of operation, in particular DDD (as a dual-chamber pacemaker) and VVI.

The pacemaker 22 is adapted in particular to act on the right and left ventricles by way of the corresponding stimulation units RVP and LVP in atrium-synchronous relationship. This means that right-ventricular and left-ventricular stimulation pulses are triggered after the expiry of an atrio-ventricular delay time (right ventricle) and an atrio-ventricular and additionally an interventricular delay time (left ventricle) respectively, which begins with an atrial event detected by the atrial detection unit AS.

Per se known mode switching into the VVI-mode at pathological atrial rates is also provided.

Adaptation of the stimulation rate at which the pacemaker 22 stimulates the ventricles and optionally the atrium to the physiological demand of the patient is preferably effected in the manner of closed-loop stimulation, by the stimulation rate being set by the control unit 30 in dependence on an integral derived from the intracardiac impedance pattern.

Finally, the control unit 30 is also adapted to monitor stimulation success by evaluation of the intracardiac impedance pattern and optionally to adapt the intensity of the stimulation pulses delivered by the stimulation units AP, LVB and RVP. That concept of capture control with adaptation of the level of stimulation intensity is known per se. The control unit 30 is also adapted to trigger a safety pulse for the situation where the intracardiac impedance pattern does not indicate stimulation success.

A second impedance detection unit 48 is provided in order to be able to already detect stimulation success during the delivery of a ventricular stimulation pulse. The unit 49 is so connected that a short-term drop in impedance in the myocardium is already to be detected during stimulation pulse delivery or shortly thereupon, and to be evaluated as an indicator in respect of stimulation success.

The range of additions to the cardiac pacemaker set forth herein also include in particular such additions for developing the cardiac pacemaker to constitute a cardioverter/defibrillator.

The invention claimed is:

1. A cardiac pacemaker comprising a stimulation pulse generator (RVP; LVP) adapted for biventricular stimulation of a heart, which is to be connected to at least one right-ventricular electrode adapted for the stimulation of a right ventricle of the heart and to at least one left-ventricular electrode adapted for the stimulation of a left ventricle of the heart and is connected to a control unit and is adapted to trigger right-ventricular and left-ventricular stimulation pulses with an interventricular delay time which is adjustable by means of the control unit, wherein the control unit is connected to an impedance detection unit which is adapted to be connected to a plurality of intercardiac electrodes and is adapted to form from an input signal formed by the impedance detection unit and dependent on an intracardiac impedance, an output signal indicating an optimum biventricular stimulation mode, wherein the control unit is adapted to adjust the interventricular delay time at which a second derivative of the pattern of the intracardiac impedance during a cardiac cycle is at the greatest.

2. A cardiac pacemaker as set forth in claim 1, wherein the control unit is adapted to trigger various biventricular stimulation modes and to evaluate the intracardiac impedance for each stimulation mode.

3. A cardiac pacemaker as set forth in claim 1, wherein the control unit is adapted to form from an input signal formed by the impedance detection unit and dependent on the intracardiac impedance, an output signal indicating an optimum interventricular delay time.

4. A cardiac pacemaker as set forth in claim 1, wherein the control unit is adapted to form from an input signal formed by the impedance detection unit and dependent on the intracardiac impedance, an output signal determining the interventricular delay time.

5. A cardiac pacemaker as set forth in claim 1, wherein the interventricular delay time is adjustable at between 20 and 40 ms.

6. A cardiac pacemaker as set forth in claim 1, wherein the stimulation pulse generator (RVP; LVP) is adapted to be connected to different ventricular electrodes or ventricular electrodes which are variable in respect of their position in the heart, wherein the control unit is adapted to evaluate intracardiac impedances for various electrode configurations or electrode positions and to indicate an optimum electrode position or configuration.

7. A cardiac pacemaker as set forth in claim 1, wherein the impedance detection unit is adapted to detect the impedance by way of voltage measurement which takes place between two electrodes of different electrode lines.

8. A cardiac pacemaker as set forth in claim 1, wherein the cardiac pacemaker is adapted to produce a current between a pacemaker housing and an intracardiac electrode for impedance measurement.

9. A cardiac pacemaker as set forth in claim 7 wherein the electrodes for voltage measurement are different from the electrodes for producing the current for impedance measurement.

10. A cardiac pacemaker as set forth in claim 8 wherein the cardiac pacemaker is adapted to produce a current for impedance measurement, which is of a substantially constant current strength of between 100 and 500 μA.

11. A cardiac pacemaker as set forth in claim 10 wherein the cardiac pacemaker is adapted to produce bi-phase current pulses for impedance measurement.

12. A cardiac pacemaker as set forth in claim 11, wherein the cardiac pacemaker is adapted to produce the bi-phase current pulses at a repetition rate of between 100 to 150 Hz.

13. A cardiac pacemaker as set forth in claim 12 wherein the cardiac pacemaker is adapted to produce bi-phase current pulses at a pulse duration of between 20 and 40 μs.

14. A cardiac pacemaker as set forth in claim 1, wherein the impedance detection unit or the control unit is adapted to average the impedance in a time window of between 50 and 300 ms duration.

15. A cardiac pacemaker as set forth in claim 14 characterized in that the impedance detection unit or the control unit is adapted to start the time window with the detection of a left-ventricular event (contraction).

16. A cardiac pacemaker as set forth in claim 14, wherein the impedance detection unit or the control unit is adapted to calculate an intracardiac impedance pattern.

17. A cardiac pacemaker as set forth in claim 14, wherein the impedance detection unit or the control unit is adapted to determine one or more of the following parameters of the intracardiac impedance pattern: $Z_{ED}$, $Z_{ES}$, $T_{ES}$, $Z_{min}$, $(Z_{ES}-Z_{ED})$, $(Z_{ES}Z_{min})$, $((Z_{ES}-Z_{min})/T_{ES})$, $((Z_{ES}-Z_{min})/(T_{ES}-T_{min}))$, $Z'_{max}$, $Z''_{max}$, $T'_{max}$ and $T''_{max}$.

18. A cardiac pacemaker as set forth in claim 17 wherein the cardiac pacemaker is in the form of a dual-chamber pacemaker with at least one ventricular and one atrial detection unit (VS, AS), for the detection of ventricular and atrial events respectively.

19. A cardiac pacemaker as set forth in claim 18 wherein the cardiac pacemaker is in the form of a rate-adaptive cardiac pacemaker in which a stimulation rate is determined on the basis of a measurement value which is characteristic of a physiological demand of a patient.

20. A cardiac pacemaker as set forth in claim 18 wherein the cardiac pacemaker is in the form of a rate-adaptive cardiac pacemaker in which a stimulation rate is set on the basis of an evaluation of the intracardiac impedance, in such a way that the variation in the intracardiac impedance is maximized.

* * * * *

UNITED STATES PATENT AND TRADEMARK OFFICE
CERTIFICATE OF CORRECTION

PATENT NO. : 7,330,759 B2
APPLICATION NO. : 10/537703
DATED : February 12, 2008
INVENTOR(S) : Carmelo Militello It is certified that error appears in the above-identified patent and that said Letters Patent is hereby corrected as shown below:

In Claim 17, column 10, line 23,
Replace "intracardiac impedance pattern: $Z_{ED}$, $Z_{ES}$, $T_{ES}$, $Z_{min}$, ($Z_{ES}$ – ..." with
--intracardiac impedance pattern: $Z_{ED}$, $Z_{ES}$, $T_{ES}$, $Z_{min}$, $T_{min}$, ($Z_{ES}$ – ...--

In Claim 17, column 10, line 24,
Replace "$Z_{ED}$), ($Z_{ES}$ $Z_{min}$), (($Z_{ES}$ – $Z_{min}$)/$T_{ES}$), (($Z_{ES}$ – $Z_{min}$)/($T_{ES}$ – ..." with
--$Z_{ED}$), ($Z_{ES}$ – $Z_{min}$), (($Z_{ES}$ – $Z_{min}$)/$T_{ES}$), (($Z_{ES}$ – $Z_{min}$)/($T_{ES}$ – ...--

Signed and Sealed this

Twenty-second Day of July, 2008

JON W. DUDAS
*Director of the United States Patent and Trademark Office*